(12) United States Patent
Tay et al.

(10) Patent No.: US 7,862,799 B2
(45) Date of Patent: Jan. 4, 2011

(54) ANTIBODY PRODUCTION METHOD

(76) Inventors: Kwang G. Tay, 15 Birdwood Avenue, Como, Western Australia 6152 (AU); William J. Penhale, 147a Bateman Road, Mount Pleasant, Australia 6153 (AU); Peter M. Geerlings, 53 Chandler Ramble, Baldivis, Western Australia 6171 (AU)

( * ) Notice: Subject to any disclaimer, the term of this patent is extended or adjusted under 35 U.S.C. 154(b) by 0 days.

(21) Appl. No.: 11/784,278

(22) Filed: Apr. 5, 2007

(65) Prior Publication Data

US 2008/0069853 A1    Mar. 20, 2008

Related U.S. Application Data

(63) Continuation of application No. PCT/AU2005/001540, filed on Oct. 6, 2005.

(51) Int. Cl.
*A61K 49/00* (2006.01)
*A61K 39/38* (2006.01)

(52) U.S. Cl. ............... 424/9.1; 424/9.2; 424/130.1; 424/184.1; 424/278.1; 424/400; 424/422; 424/423; 424/438; 424/468; 424/473; 424/489; 424/520; 424/535

(58) Field of Classification Search ........... 424/400, 424/422, 423, 438, 468, 473, 489, 9.1, 9.2, 424/130.1, 184.1, 278.1, 520, 535
See application file for complete search history.

(56) References Cited

U.S. PATENT DOCUMENTS

2002/0110555 A1* 8/2002 Lee .................. 424/130.1

OTHER PUBLICATIONS

Kemp, J.M., et al. Continuous antigen delivery from controlled relese implants induces significant and anamnestic immune responses. Vaccine, vol. 20, pp. 1089-1098, 2002.*
Liu, G.L., et al. Specific immune milk production of cows implanted with antigen-release devices. J. Dairy Sci., vol. 92, pp. 100-108, 2009.*

* cited by examiner

*Primary Examiner*—Rodney P. Swarttz
(74) *Attorney, Agent, or Firm*—Kathleen M. Williams; Gabriel J. McCool; Edwards Angell Palmer & Dodge LLP

(57) ABSTRACT

A method of inducing the sustained release of antibodies in milk comprising the step of: a) implanting at least one antigen releasing device adjacent to, within close proximity of or within at least one supramammary lymph node, wherein in use the antigen releasing device releases an antigen into the tissue area around the supramammary lymph node which stimulates antibody secretion into a mammary gland.

29 Claims, 11 Drawing Sheets

ANTIBODY PRODUCTION METHOD

This application is a Continuation of International Application No. PCT/AU2005/001540, filed Oct. 6, 2005, which claims priority to Australian Application No. 2004905762, filed Oct. 6, 2004. The entire contents of the foregoing applications are incorporated herein in their entirety.

FIELD OF THE INVENTION

The present invention relates to a method for inducing a sustained production of antibodies or immunoglobulins. More particularly, it relates to a method of inducing a sustained production of antibodies in the milk of a mammal.

BACKGROUND ART

The advantage of producing antibodies in milk over the traditional source of antibodies from blood lies in the constancy of supply through the daily access to milk. After blood products are harvested, the production animal is allowed to recover for extended periods (for example, up to one month). Hence, the yield of antibodies is limited (approximately 3 to 30 mg per month) due to the finite amount of blood that can be obtained. In contrast, for example, dairy animals milked daily results in significant increases in yield (e.g. 2 mg per day multiplied by 30 days, gives 150 mg per month).

Injections or infusions directly into the teat of the mammal have previously been used to stimulate the production of antibodies in milk. Such examples are set out in the following literature: J. L. Smith, J. S Hogan & K. L Smith (1999) "Efficacy of intramammary immunization with an *Escherichia coli* JS bacteria." Journal of Dairy Science, 82:2582-2588; J. S Hogan, K. L Smith, P. Schoenberger, S. Romig & L Thompson (1997) "Response of antibody titers to intramammary immunization with *Escherichia coli* JS bacteria." Journal of Dairy Science, 80: 2398-2402; F. J Bourne, T. J Newby & J. W Chidlow (1975) "The influence of route of vaccination on the systemic and local immune response in the pig." Research in Veterinary Science, 18:244-248. Such injections are time consuming as they must be repeated to re-stimulate antibody production. Furthermore, injection directly into the teat of a mammal frequently results in infections such as mastitis.

Intramammary immunization techniques have generally not been preferred as a route for vaccination under field conditions due to the high chance of mammary infection (R. F. Sheldrake (1987) Australian Journal of Dairy Technology, 42:30-32) and often requires application by highly skilled practitioners.

It should be noted that much of the published literature concerning immunoglobulin production in mammary gland secretions is directed to disease prevention (that is, vaccination) in animals or their offspring. Few are directed to the production of immunoglobulin enriched milk for the purposes of obtaining the immunoglobulins themselves.

SUMMARY OF THE INVENTION

In a first aspect of the invention, there is provided a method for inducing the sustained release of antibodies in milk comprising the step of: implanting at least one antigen releasing device adjacent to or within at least one supramammary lymph node, wherein in use the antigen releasing device releases an antigen into the tissue area around the supramammary lymph node which stimulates antibody secretion into a mammary gland.

According to a second aspect the invention also provides antibodies produced by any one of the methods of the present invention.

According to a third aspect the present invention relates to a method for the production of milk containing antibodies which method comprises induction of antibodies according to the method detailed above and then collecting the antibody containing milk from the mammal. The collection of milk may be effected using normal milking processes.

Other objects, features, and advantages of the instant invention, in its details as seen from the above, and from the following description of the preferred embodiment will become apparent to those skilled in the art.

DISCLOSURE OF THE INVENTION

General

Figure 1:
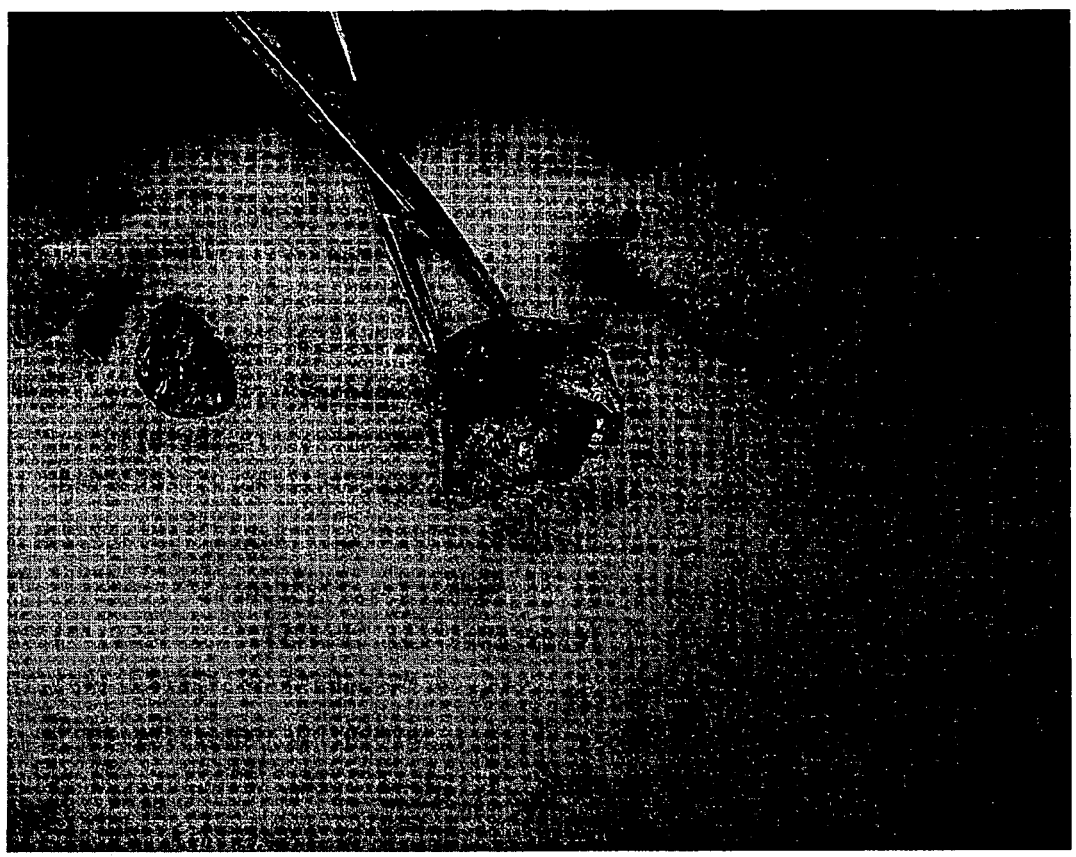
FIG. 1 shows a photograph of the supramammary gland stained blue due to migration of dye inoculated in the groin area of the animal (photo courtesy of Dr Martin CAKE, Anatomy Department Murdoch University).

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively and any and all combinations or any two or more of the steps or features.

Each document, reference, patent application or patent cited in this text is expressly incorporated herein by reference, which means that it should be read and considered by the reader as part of this text. That the document, reference, patent application or patent cited in this text is not repeated in this text is merely for reasons of conciseness.

The present invention is not to be limited in scope by the specific embodiments described herein, which are intended for the purpose of exemplification only. Functionally equivalent products, compositions and methods are clearly within the scope of the invention as described herein.

Throughout this specification, unless the context requires otherwise, the word "comprise", or variations such as "comprises" or "comprising", will be understood to imply the inclusion of a stated integer or group of Integers but not the exclusion of any other integer or group of integers.

Through this specification the acronyms CRD and ARD are used interchangeably. Both refer to the antigen releasing device described, disclosed and claimed herein.

Other definitions for selected terms used herein may be found within the description of the invention and apply throughout. Unless otherwise defined, all other scientific and technical terms used herein have the same meaning as commonly understood to one of ordinary skill in the art to which the invention belongs.

DETAILED DISCLOSURE OF THE INVENTION

This invention is based on the unexpected discovery that a sustained release of antibodies in milk can be achieved by stimulating the supramammary lymph node over a long period with antigen released from an implanted antigen releasing device implanted adjacent to, within close proximity of or within the supramammary gland. The advantage of stimulating the supramammary lymph node lies in the proximity of the node to the mammary glands. Antibodies produced by the supramammary lymph node are secreted into the mammary glands and therefore enter the milk of the mammal. The present method causes stimulation of antibody production that can be maintained over long periods by the slow release of antigen from the antigen releasing device. The method stimulates the production of different subclasses or isotypes of immunoglobulin, such as IgA, IgG and IgM.

Thus, in a first aspect of the invention, there is provided a method for inducing the sustained release of antibodies in milk comprising the step of: implanting at least one antigen releasing device adjacent to, within close proximity of or within at least one supramammary lymph node, wherein in use the antigen releasing device releases an antigen into the tissue area around the supramammary lymph node which stimulates antibody secretion into a mammary gland.

According to this invention the distance of the implant from the supramammary gland should be at least close enough that the release of antigen from the antigen releasing device causes the antibody response of the mammal (into which it is implanted) to be maintained at a level that facilitates the production of antibodies in milk at levels that are therapeutically or anti-microbially suitable. For examples, the ARD may be implanted in the udder. Alternatively, by way of illustration the antigen releasing device is preferably implanted at a distance of up to 100 mm from at least one supramammary lymph node, wherein in use the antigen releasing device releases an antigen into the tissue area around the supramammary lymph node which stimulates antibody secretion into a mammary gland. Preferably, the antigen releasing device is implanted adjacent to or at a distance of between about 1 mm and 100 mm from the supramammary lymph node. Most preferably, the distance is between about 50 mm and 100 mm.

It will be appreciated that the present invention may be used to stimulate antibody production in a number of glands in an animal. In this respect immunization at one gland has been shown to result in antibody activity in secretions by other mammary glands (see, for example, F. J Bourne et al (1975) Research in Veterinary Science 18:244-248).

The method of the present invention is performed on mammals. Preferably, the mammals used in the method are rodents or ruminants. Most preferably, the mammals are goats, sheep or cattle. Desirably the mammals are dairy cattle breeds; however dairy goat or sheep breeds may also be used.

The term "milk" used herein refers to both milk and colostrum in the form in which it is produced by the mammal or any derivative of whole milk, such as skimmed milk or whey, in liquid or in solid form.

The term "antigen" as used herein refers to any material capable of inducing an antigenic response in a treated mammal. Antigens may be selected according to the ultimate utility of the antibodies. That is, if the antibodies are to be used for generating passive immunity, the antigen against which such immunity is sought should be used may be derived from bacteria, viruses, yeasts, mycoplasmas, proteins, haptens, peptides, animal tissue extracts, plant tissue extracts, fungi, pollens, dust, chemical antigens intact mammalian cells (including spermatazoa) and fractions of cells. Where haptens or peptides are to be used as antigens these should first be conjugated to carrier substances such as proteins using chemistry well known to people versed in the art (Hanly et al; Review of Polyclonal Antibody Production Procedures, ILAR Journal (1995), 37:3, 93-118).

In one embodiment of the invention any bacterial antigen may be used in the invention. Preferably, the bacterial antigens are desirably selected from the bacterial species selected from, but no limited to: *Escherichia, Staphylococcus, Streptococcus, Salmonella* and *Helicobacter*. Particularly preferred bacterial species are *Escherichia coli, Clostridium difficile, Vibrio cholerae* and *Helicobacter pylori* and *Pseudomonas fluorescens*. Most preferably, the antigen is lipoprotein lipase from *Pseudomonas fluorescens*.

Implantation of the antigen releasing device adjacent to or within at least one supramammary lymph node causes the antigen contained in the antigen releasing device to be released into the tissue near and within the node (FIG. 1). This in turn stimulates the node to generate antibodies to the antigen. These antibodies are secreted into the mammary glands and therefore enter the milk of the mammal.

The size, characteristics and choice of antigen releasing device is dependant on the size and properties of the antigen of interest. It is desirable that the choice of antigen releasing device allows the antigen contained therein to be released from the device at a rate which causes the antibody response of the mammal into which it is implanted to be maintained at a desirable level.

Devices for slow release of compositions are described in, for example, U.S. Pat. No. 3,279,996, whilst immunopotentiating devices for the sustained release of antigen are described, for example, in Australian Patent No. 740133

A porous silicon implant impregnated with a beneficial substance is described in Patent No. DE69917625D. An implantable device for molecule delivery is described in U.S. Pat. No. 6,716,208. Other suitable examples of sustained-release preparations include semipermeable matrices of solid hydrophobic polymers containing the protein, which matrices are in the form of shaped articles, e.g., films, or microcapsules compressed into delivery devices. Examples of sustained-release matrices include polyesters, hydrogels [e.g., poly(2-hydroxyethyl-methacrylate) as described by Langer et al., J. Biomed. Mater. Res. 15:167-277 (1981) and Langer, Chem. Tech. 12:98-105 (1982) or poly(vinylalcohol)], polylactides (U.S. Pat. No. 3,773,919, EP 58,481), copolymers of L-glutamic acid and gamma ethyl-L-glutamate (Sidman et al., Biopolymers 22:547-556 [1983]), non-degradable ethylene-vinyl acetate (Langer et al., supra), degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid (EP 133,988). Another reference is B. Baras, M. A. Benoit & J. Gillard (2000) "Parameters influencing the antigen release from spray dried poly (DL-lactide) microparticles." International Journal of Pharmaceutics, 200:133-145.

While polymers such as ethylene-vinyl acetate and lactic acid-glycolic acid enable release of molecules for over 100 days, certain hydrogels release proteins for shorter time periods. When encapsulated antigens remain in the body for a long time, they may denature or aggregate as a result of exposure to moisture at 37° C., resulting in a loss of biological activity and possible changes in immunogenicity. Rational strategies can be devised for antibody stabilization depending on the mechanism involved. For example, if the aggregation mechanism is discovered to be intermolecular SS or disulfide bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release fragment compositions also include liposomally entrapped fragments. Liposomes containing the antibody are prepared by methods known per se: DE 3,218,121; Epstein et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30% cholesterol, the selected proportion being adjusted for the optimal antibody therapy. Other devices for the slow release of antigen into the tissue near the supramammary lymph node are encompassed within the present invention.

An effective amount of antigen to be employed therapeutically will depend, for example, upon the objectives, the route of administration, the type of antigen and/or adjuvant and the condition of the animal. Accordingly, it will be necessary for the therapist to titre the dosage and modify the mode of administration as required to obtain the optimal effect. Typically, the operator will administer an antigen until a dosage is reached that achieves the desired effect. The progress of this therapy is easily monitored by conventional assays.

In the further aspect of the invention, there is provided a method for inducing the sustained release of antibodies in milk comprising the further step of administering a primer composition by an administration route selected from intramammary, intraperitoneal, intramuscular or intranasal. Administration of a primer may take place before, during or after implanting the antigen releasing device. It is preferable that the primer composition be delivered to a mucosal surface so that antibody production on mucosal surfaces (of which the mammary gland is one) is preferentially stimulated.

The primer composition administration could be a single administration, or could comprise a number of administrations at intervals over a period of days or weeks. Timing of the administration of primer composition is generally spaced based on contemporary immunization protocols (for example, every 2 weeks). To avoid local irritation and congestion, it is usually preferred that the primer composition not be administered to the same site more frequently than every second week. The initial exposure of this priming step stimulates the low level production of antibodies, which production is then increased and maintained by antigen released by the antigen releasing device.

The method of the present invention may also comprise the additional step of administering a booster composition comprising antigen to a mammal by an administration route selected from intramammary, intraperitoneal, intramuscular and/or intranasal after the antigen releasing device has been implanted. It is preferable that the booster composition be delivered to a mucosal surface so that antibody production on mucosal surfaces (of which the mammary gland is one) is preferentially stimulated.

Such booster compositions could be administered as a single administration, or could comprise a number of administrations at intervals over a period of days or weeks. Administration of booster compositions is generally spaced to suit the convenience of the operator. To avoid local irritation and congestion, it is usually preferred that administration of the booster composition to the same site not be more frequent than every other week.

In a preferred method, the antigen administered is the same for each step of the method. Therefore, the same antigen may be used in the antigen releasing device, the primer composition and/or the booster composition.

The use of adjuvants both within the antigen releasing device and in the compositions used for priming and boosting is also desirable. An adjuvant can serve as a tissue depot that slowly releases the immunogen and also as a lymphoid system activator that non-specifically enhances the immune response [Hood et al., in *Immunology*, p. 384, Second Ed., Benjamin/Cummings, Menlo Park, Calif. (1984)]. Suitable adjuvants for use with the antigens of the invention include but are not limited to the following: Freund's complete adjuvant (FCA), Freund's incomplete adjuvant (FIC), TiterMax Gold™, adjuvant 65, cholera toxin B subunit, IL1-B Fragment 163-171 synthetic human adjuvant, alhydrogel; or *bordetella pertussis*, muramyl dipeptide, cytokines, saponin, Adju-Phos, Algal Glucau, Algammuliu, Alhydrogel, Antigen Formulation, Avridine, Bay R1005, calcitrial, calcium phosphate, Gel, CRL 1005, cholera Holotoxin (CT), DDA, DHEA, DMPC, DMPG, DOC/Alum Complex, Gamma Inulin, Gerbu Adjuvant, GMDP, Imiquimod, Imuither, Interferon-gamma, ISCOM(s), Iscoprop 7.0.3, Loxoribine, LT-OA or LT Oral adjuvant, MF59, MONTANIDE ISA51 and ISA720, MPL, MTP-PE, MTP PE Liposomas, murametide, murapalmitive, NAGO, Nonionic surfactant vesides, Pleuram, PLGA, PGA and PLA, Pluronic L121, PMMA, PODDS, Poly Ra, Polyru Polyphophazene, Polysorbate 80, Protein Cochleates, QS-21, Quil A, Rehydrogel HPA, Rehydrogel LV, S-28465, SAF-1, Sclavo, peptide, Seudai Protediposomes, sendai-containing lipid matrices, Span 85, specal, squalene, stearyl Tyrosine, Theramide, Threonyl-MDP, Ty Particles, saponin Q521, MF59 and Alum.

In a further aspect of the invention, the method further comprises a preselection step. In this step individual animals are tested and selected for their ability to produce antibodies. Considerable between-animal variability exists for the production of antibodies. This preselection step, wherein the animals showing the best antibody titre responses are selected, assists in decreasing the between-animal variability factor. This process may similarly be used to build groups of animals particularly suited to antibody production.

In relation to the step of administering the priming composition or the boosting composition, preferably the antigenic substances are suspended in liquid medium for infusion or injection according to known protocols. Any appropriate carriers, diluents, buffers, and adjuvants known in the art may be used. Suitable suspension liquids include saline solution, water, and physiologic buffers.

If administration of the priming composition or the boosting composition is by injection, preferably prior to injection the antigens are emulsified in appropriate carriers with adjuvant using, for example, a laboratory homogenizer. In one example of such a method, aqueous antigen is mixed with 3 volumes of adjuvant and emulsified until a stable water-in-oil emulsion is formed. The presence of a stable emulsion can be demonstrated using tests well known in the art.

According to a second aspect, the invention also provides antibodies produced by any one of the methods of the present invention and fragments of such antibodies. The antibodies may be of any of the different subclasses or isotypes of immunoglobulin, eg IgA, IgG or IgM, or any of the other subclasses.

Exemplary antibody molecules and fragments that may be prepared according to this aspect of the invention include intact immunoglobulin molecules, substantially intact immunoglobulin molecules and those portions of an immunoglobulin molecule that contain the paratope. Such portion of antibodies that contain the paratope include those portions known in the art as Fab, Fab', F(ab')$_2$ and F(v). Fab and F(ab')$_2$. These portions of antibodies may be prepared by the proteolytic reaction of papain and pepsin, respectively, on substantially intact antibodies by methods that are well known. See for example, U.S. Pat. No. 4,342,566. Fab' antibody portions are also well known and are produced from F(ab')$_2$ portions followed by reduction of the disulfide bonds linking the two heavy reduction of the disulfide bonds linking the two heavy chain portions as with mercaptoethanol, and followed by alkylation of the resulting protein mercaptan with a reagent such as iodoacetamide. Preferably the antibodies are intact antibody molecules, and are utilized as illustrative herein.

According to a third aspect the invention relates to a method for the production of mammalian milk containing antibodies, which method comprises induction of antibodies according to the method detailed above and then collecting the antibody containing milk from the mammal. The collection of milk may be effected using normal milking processes.

This milk is useful in the form obtained directly from the mammal, but may be processed if required. Examples of processing steps include heat treatment, ultra violet radiation, concentration, supplementation with food additives, drying into concentrates, milk or whey powders and the like.

As a further step to the method of the invention, the antibodies may be isolated from the milk. Isolation may be effected using separation techniques known in the art. For example, methods for the isolation of immunoglobulin rich fractions from whey (Nielson, K. (1986) Can. J. Vet. Res 50: 227-231; EP 0320152; WO 97/27757; GB2 179947) from milk (Kanamara et al (1993) Milchwissenschaft 48:247-251; U.S. Pat. No. 4,229,342), from colostrum (Kanamaru et al (1982) Agric. Biol. Chem. 46:1531-1537, French Patent No. 2520235, New Zealand Patent No. 239466 and U.S. Pat. No. 4,582,580), and from milk and colostrum (U.S. Pat. No. 4,644,056) are known.

The isolated antibodies may subsequently be purified if desired. Purification may be carried out according to known techniques such as precipitation and ion exchange chromatography. Suitable techniques are disclosed in the journals and patents referenced above. Both the isolated and purified antibodies produced in accordance with the additional process steps also form part of the present invention.

Methods for producing protein concentrates containing antibodies on a commercial scale are disclosed in Swiss Patent No. 1,573,995 incorporated herein by reference. Briefly, the method comprises collecting the milk of hyperimmunized milk-bearing females; separating the cream and the impurities, coagulating the clarified and skimmed milk, separating the casein, filtering, ultrafiltering and sterilizing the proteins of the whey by filtration, evaporating and drying the product under conditions which do not denature the antibodies and which maintain sterility. as set out above.

EXAMPLES

Further features of the present invention are more fully described in the following non-limiting examples. It is to be understood, however, that this detailed description is included solely for the purposes of exemplifying the present invention. It should not be understood in any way as a restriction on the broad description of the invention as set out above.

Example 1

Preparation of Antigen Releasing Device Minus Adjuvant

Materials
(i) 0.15 g mannitol-D (Sigma-Aldrich)
(ii) 0.15 g sodium citrate (Proanalys)
(iii) 11.25 mg lipase from *Pseudomonas fluorescens* (Sigma-Aldrich)
(iv) 0.75 ml part A Silastic (Dow Corning Q74850)
(v) 0.75 ml part B Silastic (Dow Corning Q7-4850)

(vi) 2×2.5 ml disposable syringes (Terumo)
(vii) 2×1 ml syringe (Terumo)
(viii) 2×12G×4 inch stainless steel hypodermic needles
(ix) 37° C. incubator
(x) sterile petri dish
(xi) sterile scalpel
(xii) sterile spachella
(xiii) 32 ml glass McCartney bottle Methods (i) Remove pistons from all syringes
(ii) Part A silastic placed into 1 ml syringe using spatula. Piston replaced into syringe and 0.75 ml quantity dispensed into one 2.5 ml syringe. Procedure repeated for Part B.
(iii) Lipase, mannitol and sodium citrate are combined and mixed in a small glass McCartney then placed into the 2.5 ml syringe containing part A of the silastic. Part B was then expelled from its syringe into the other 2.5 ml syringe effectively 'sandwiching' the lipase, mannitol and sodium citrate between part A and part B of the silastic in one syringe. The piston was replaced in this syringe and removed from the empty syringe. The contents of the first syringe were expelled into the second syringe then its piston replaced. The procedure was repeated 20 times to effectively mix all reagents. The reagents were finally expelled into two 12G needles and stored at 37° C. for three days. The cured silastic was extracted from the needles, cut into 3 cm lengths in the open petri dish and placed under UV light for 24 hours before being stored in sterile 10 ml centrifuge tubes at −20° C. Each 3 cm ARD contained 1 mg lipase, 13 mg mannitol, 13 mg sodium citrate, in 250 μl of total silastic.

Example 2

Preparation of Antigen Releasing Device Including Adjuvant

Materials (i) 0.3 g mannitol-D (Sigma-Aldrich)
(ii) 0.3 g sodium citrate (Proanalys)
(iii) 22.50 mg lipase from *Pseudomonas fluorescens* (Sigma-Aldrich)
(iv) 1.2 mg IL1-B Fragment 163-171 synthetic human (Sigma)
(v) 1.5 ml part A Silastic (Dow Corning Q7-4850)
(vi) 1.5 ml part B Silastic (Dow Corning Q7-4850)
(vii) 2×2.5 ml disposable syringes (Terumo)
(viii) 2×1 ml syringe (Terumo)
(ix) 2×12G×4 inch stainless steel hypodermic needles
(x) 37° C. incubator
(xi) sterile petri dish
(xii) sterile scalpel
(xiii) sterile spachella
(xiv) 32 ml glass McCartney bottle Methods (i) Remove pistons from all syringes
(ii) Part A silastic placed into 1 ml syringe using spatula. Piston replaced into syringe and 0.75 ml quantity dispensed into one 2.5 ml syringe. Procedure repeated for Part B.

Lipase, mannitol and sodium citrate mixed in a small glass McCartney then placed into the 2.5 ml syringe containing part A of the silastic. Part B was then expelled from its syringe into the other 2.5 ml syringe effectively 'sandwiching' the lipase, mannitol and sodium citrate between part A and part B of the silastic in one syringe. The piston was replaced in this syringe and removed from the empty syringe. The contents of the first syringe was expelled into the second syringe then its piston replaced. The procedure was repeated 20 times to effectively mix all reagents. The reagents were finally expelled into two 12G needles and stored at 37° C. for three days. The cured silastic was extracted from the needles, cut into 3 cm lengths in the open petri dish and placed under UV light for 24 hours before being stored in sterile 10 ml centrifuge tubes at −20 deg C. Each 3 cm ARD contained 1 mg lipase, 13 mg mannitol, 13 mg sodium citrate, 50 μg IL1-B, in 250 μl of total silastic.

Example 3

Delivery of ARD

Figure 5:
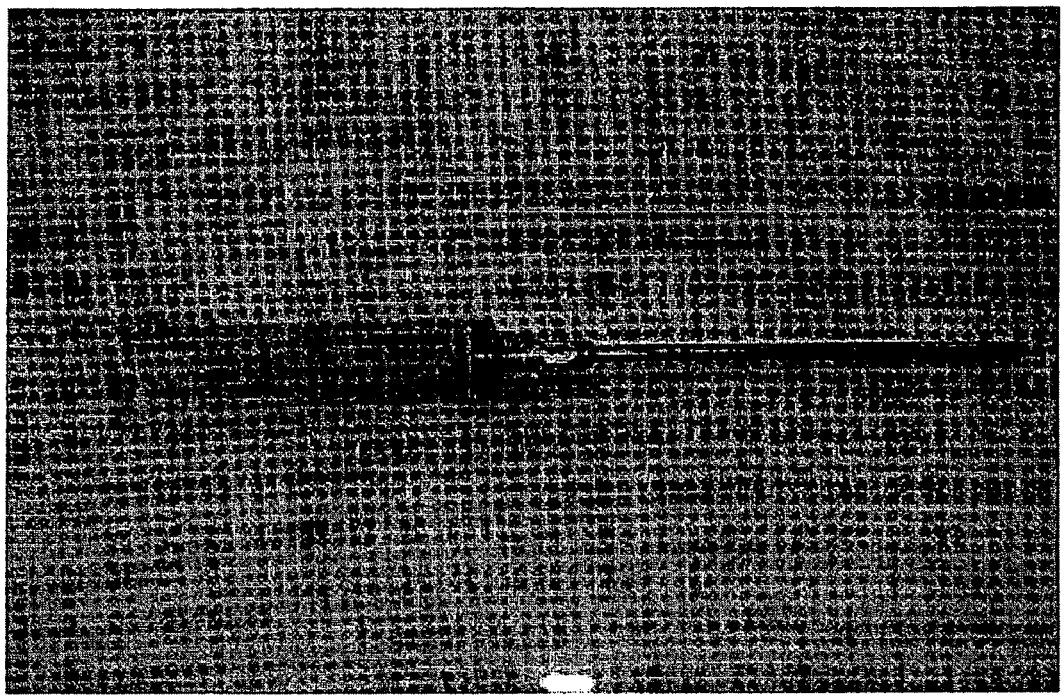
FIG. 5 shows a schematic diagram of the apparatus used to implant the antigen releasing device.
Figure 6:
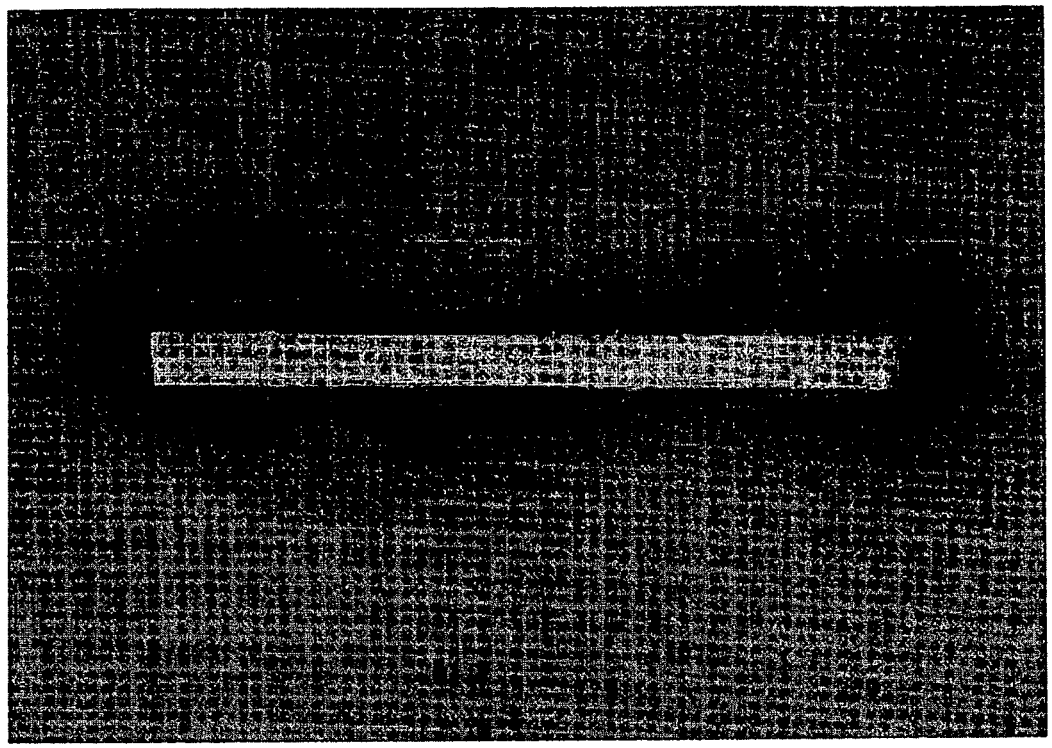
FIG. 6 shows a photograph of the diffusion of a lipase protein from an antigen releasing device in accordance with an aspect of the present invention into a milk agar plate. As the enzyme diffuses from the pores of the tube, it hydrolyzes the lipids in the milk agar, as evident from the dark zones around the rod. The lipase protein was used as the model antigen for the development of the invention.

A device was purpose designed and built comprising 10 ml disposable luer lock syringe, 10G×4 inch stainless steel hypodermic needle and a 90 mm×10G stainless steel welding rod (see FIG. 5 below). The device was assembled with the rod attached to the piston of the syringe and passing through the needle. The piston was withdrawn about 3 cm allowing for free space near the tip of the needle in which to insert the antigen releasing device. Thus, when the piston is depressed, the antigen releasing device is expelled from the needle by the rod (see FIG. 5 below).

The animal was placed on the floor on its back and restrained by animal handlers. An area approximately 3 cm×10 cm right lateral and adjacent to the udder was swabbed with iodine. 2 ml of 2% lignocaine infiltrated the cutaneous tissue through a 26G hypodermic needle as a local anaesthetic. The 10G needle housing the ARD was inserted in the posterior end of this area and pushed to the anterior end subcutaneously. The piston was depressed and needle withdrawn simultaneously. The point of insertion was swabbed with iodine. In most cases the antigen releasing device could be felt in situ.

Example 4

Preparation of Lipase Nasal Inoculum

Materials (i) 15.5 mg lipase from *P. fluorescens* (Sigma-Aldrich)
(ii) 38.75 ml 0.85% saline (Excel laboratories)
(iii) 1 mg Cholera Toxin B Subunit (US Biological)
(iv) 2.5 ml syringes
(v) 50 ml sterile tube (Falcon)
(vi) 8-10 cm length of approximate 20G plastic tube from winged infusion set (Terumo)

Methods (i) All reagents were combined in 50 ml tube on day of first administration.
(ii) The remainder was stored at 4° C. until used.

Example 5

Figure 2:
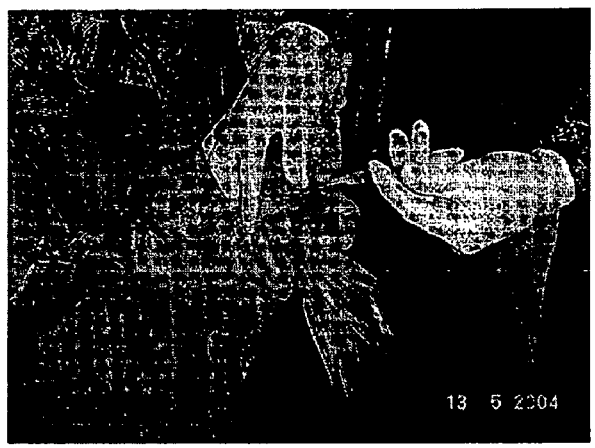
FIG. 2 shows a photograph of the intranasal immunization of a goat.
Figure 3:
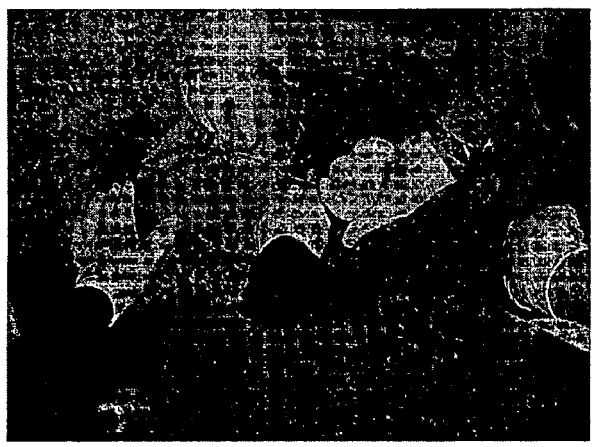
FIG. 3 shows a photograph of the implantation of an antigen releasing device in accordance with an aspect of the present invention into the groin of a sheep.
Figure 4:
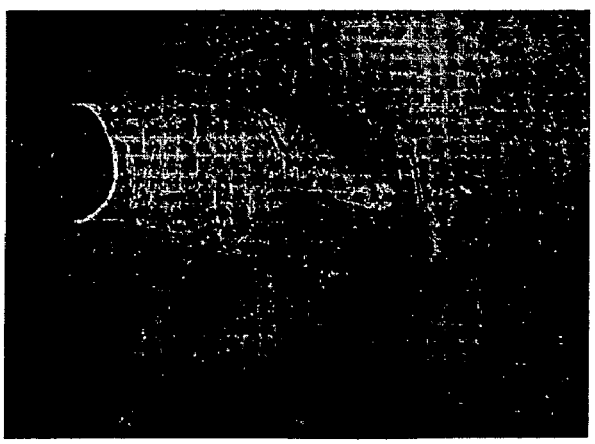
FIG. 4 shows the location of the implanted antigen releasing device of FIG. 3 in the sheep.

Delivery of Nasal Inoculum 2.5 ml of inoculum (containing 1 mg lipase, 64.5 μg Cholera Toxin B Subunit) was drawn into syringe with the 20G tube from the infusion set attached. 60-80% of tube length was placed into right nostril of animal and slowly dispensed whilst simultaneously withdrawing the tube from the nostril (see FIG. 2).

Example 6

Preparation of Lidase Intramuscular Injected Inoculum

Materials
(i) 36.5 mg of lipase from *P. fluorescens* (Sigma)
(ii) 9.1 ml of 0.85% saline (Excel Laboratories)
(iii) TiterMax Gold™ adjuvant
(iv) glass McCartney bottle
(v) 3 ml all plastic syringes (Teruma)
(vi) stainless steel double-hub
(vii) 23G×1 inch hypodermic needle Methods
(i) lipase and saline were combined in glass McCartney giving a concentration of 4 mg/ml on the day of first administration. The remainder was stored at 4° C. until required.

Example 7

Delivery of Intramuscular Inoculum 0.5 ml of 4 mg/ml lipase in saline solution as drawn into syringe and emulsified with 0.5 ml TiterMax Gold™ as per manufacturers instructions. Inoculum was administered intramuscularly (IM) in the rear of the left hind leg using 23G×1 inch needle attached to the syringe. Animals received IM injections Day 7, Day 14 and Day 21.

Example 8

Immunisation Protocol 1

The animals were given an IM injection in the upper hind limb (rump).

Five animals were immunized with four different antigens. Two animals each received one type of antigen and the remaining three animals received a different antigen each. Table 1 summarizes the schedule of the primary inoculums and two subsequent boosts, and the concentrations of antigen (Ag), and volumes of the TiterMax adjuvant (T/max).

TABLE 1

Immunogen composition and inoculation schedule for goats inoculated with a variety of antigens.
Goat Inoculation Schedule

| | | PRIMARY INOCULATION | | | | | |
|---|---|---|---|---|---|---|---|
| Tag | Antigen | Primary | Ag (μg) | Ag(μl) | T/Max(μl) | Tot (μl) | Bleed y/n |
| X0247 | *P. fluorescens* lipase | 28 Nov. 2003 | 1250 | 250 | 750 | 1000 | Y |
| X0248 | *P. fluorescens* lipase | 28 Nov. 2003 | 1250 | 250 | 750 | 1000 | Y |
| X0241 | Type X protease | 17 Mar. 2004 | 500 | 500 | 500 | 1000 | Y |
| X0242 | Type XVII-B protease | 17 Mar. 2004 | 500 | 500 | 500 | 1000 | Y |
| X0243 | Type VIII protease | 17 Mar. 2004 | 500 | 500 | 500 | 1000 | Y |
| | | SECONDARY INOCULATION | | | | | |
| Tag | Antigen | S'dary | Ag (μg) | Ag(μl) | T/M(μl) | Tot (μl) | Bleed y/n |
| X0247 | *P. fluorescens* lipase | 10 Dec. 2003 | 950 | 190 | 560 | 750 | Y |
| X0248 | *P. fluorescens* lipase | 10 Dec. 2003 | 950 | 190 | 560 | 750 | Y |
| X0241 | Type X protease | 1 Apr. 2004 | 500 | 500 | 500 | 1000 | Y |
| X0242 | Type XVII-B protease | 1 Apr. 2004 | 500 | 500 | 500 | 1000 | Y |
| X0243 | Type VIII protease | 1 Apr. 2004 | 500 | 500 | 500 | 1000 | Y |
| | | TERTIARY INOCULATION | | | | | |
| Tag | Antigen | Tertiary | Ag (μg) | Ag(μl) | T/M(μl) | Tot (μl) | Bleed y/n |
| X0247 | *P. fluorescens* lipase | 22 Dec. 2003 | 2500 | 500 | 500 | 1000 | Y |
| X0248 | *P. fluorescens* lipase | 22 Dec. 2003 | 2500 | 500 | 500 | 1000 | Y |
| X0241 | Type X protease | 16 Apr. 2004 | 500 | 500 | 500 | 1000 | Y |
| X0242 | Type XVII-B protease | 13 May 2004 | 500 | 500 | 500 | 1000 | N |
| X0243 | Type VIII protease | 16 Apr. 2004 | 500 | 500 | 500 | 1000 | Y |

Example 9

Immunization Protocol 2

The animals were given antigen inoculation by antigen releasing device (ARD) and/or injection.

Table 2 summarizes the schedule of inoculums and refers to 6 animals and one antigen.

One animal received a sub-cutaneous Injection in the groin on Day 0 of the antigen and on Day 30 the same animal received an IM injection of the antigen. One animal received a sub-cutaneous injection of the antigen on Day 0 only. One animal received an implant having the antigen in the groin on Day 0. One animal received an implant having the antigen in the groin on Day 0 and on Day 30 received an IM injection of the antigen in the rump. Two animals received an implant having antigen in the groin on Day 0 and on Day 15 one received a nasal and the other an IM injection boost.

TABLE 2

Protocols for initial trial of antigen releasing device (ARD).
Trial CRD and S/C injection of Ag to assess Ab secretion via mammary

| Date | Tag | Ag | Amount | Adjuvant | Amount | Delivery | Total Vol | Location | Milk y/n | Bleed y/n |
|---|---|---|---|---|---|---|---|---|---|---|
| 28 Apr. 2004 | White 651 8RS | Lipase | 2.5 mg | T/Max | 500 ul | S/C | 1 ml | groin | Y | Y |
| 28 Apr. 2004 | Black 1292 BX8 | Lipase | 2.5 mg | T/Max | 500 ul | S/C | 1 ml | groin | Y | Y |
| 28 Apr. 2004 | Black 1675 BX8 | Lipase | 250 ug unsheathed silastic CRD | | | S/C | | RH groin | Y | Y |
| 28 Apr. 2004 | White 552 8RS | Lipase | 250 ug sheathed silastic CRD | | | S/C | | RH groin | Y | Y |
| 13 May 2004 | White 651 8RS | Lipase | 0 | 0 | 0 | 0 | 0 | 0 | Y | Y |
| 13 May 2004 | Black 1292 BX8 | Lipase | 0 | 0 | 0 | 0 | 0 | 0 | Y | Y |
| 13 May 2004 | Black 1675 BX8 | Lipase | | CRD | | | | | Y | Y |
| 13 May 2004 | White 552 8RS | Lipase | | CRD | | | | | Y | Y |
| 13 May 2004 | White 367 | lipase | 1 mg/12 mg mannitol/12 mg SC-CRD | | | | 30 × 2 mm | Rh groin | Y | Y |
| 13 May 2004 | Orange 468 | lipase | 1 mg/12 mg mannitol/12 mg SC-CRD | | | | 30 × 2 mm | Rh groin | Y | Y |
| 28 May 2004 | White 651 8RS | Lipase | 2.5 mg | T/Max | 500 ul | S/C | 1 ml | RH rump | Y | Y |
| 28 May 2004 | Black 1292 BX8 | Lipase | 0 | 0 | 0 | 0 | 0 | 0 | Y | Y |
| 28 May 2004 | Black 1675 BX8 | Lipase | 0 | 0 | 0 | 0 | 0 | 0 | Y | Y |
| 28 May 2004 | White 552 8RS | Lipase | 2.5 mg | T/Max | 500 ul | S/C | 1 ml | RH rump | Y | Y |
| 28 May 2004 | White 367 | lipase | 2.5 mg in 2.5 ml saline | | | | 2.5 ml | nasal | Y | Y |
| 28 May 2004 | Orange 468 | lipase | 2.5 mg | T/Max | 500 ul | S/C | 1 ml | Lhrump | Y | Y |

| Date | Tag | Ag | Milk y/n | Bleed y/n |
|---|---|---|---|---|
| 1 Jul. 2004 | White 367 | lipase | Y | Y |
| 1 Jul. 2004 | Orange 468 | lipase | Y | Y |

Example 10

Immunization Protocol 3

Protocols used 2 animals per group with 12 goats used in total.

Six different protocols were evaluated in two separate animals to determine an optimal procedure to produce sustained antibody levels in milk, summarized in Table 4 and 5.

TABLE 4

The immunization protocols used to stimulate the production of antibodies in milk.

| | | Innoculation Protocol | | | | Sampling Frequency | |
|---|---|---|---|---|---|---|---|
| Group Description | | Adjuvant | Day 1 | Day 7 | Day 14 | Day 21 | Milk Collection | Blood Collection |
| 1 | Intramuscular (IM) Injection only | YES | | IM Injection | IM boost | IM injection | Daily | 3-4 day intervals |
| 2 | ARD only | YES | Implant ARD | | | | Daily | 3-4 day intervals |
| 3 | Intranasal (IN) spray only | YES | | IN Innoculation | IN boost | IN boost | Daily | 3-4 day intervals |
| 4 | Intramuscular (IM) Injection + ARD | YES | Implant ARD | IM Injection | | | Daily | 3-4 day intervals |
| 5 | Intranasl (IN) spray | YES | | IM Injection | IM boost | IM injection | Daily | 3-4 day intervals |
| 6 | ARD only | NO | Implant ARD | | | | Daily | 3-4 day intervals |

TABLE 5

The immunization protocols used to stimulate
the production of antibodies in milk.

| S/Mark | Inoculum | Amount | Delivery | Site | Freq |
|---|---|---|---|---|---|
| Group 1—Inject. | | | | | |
| | lipase | 2.0 mg | I.M | R/h quart | Day 7 |
| | TiterMax | 500 ul | | | Day 14 |
| | saline | 500 ul | | | Day 21 |
| Group 2—CRD Ino Adj | | | | | |
| | lipase | 1 mg | CRD | RH groin | Day 0 |
| | mannitol | 13 mg | | | |
| | sod citrate | 13 mg | | | |
| | IL-1B | 50 ug | | | |
| | silastic | 250 ul | | | |
| Group 3—nasal only | | | | | |
| | lipase | 1 mg | nasal | nostril | Day 7 |
| | C/Tox | | | | Day 14 |
| | saline | 2.5 ml | | | Day 21 |
| Group 4—CRD & Inj | | | | | |
| | lipase | 1 mg | CRD | RH groin | Day 0 |
| | mannitol | 13 mg | | | |
| | sod citrate | 13 mg | | | |
| | IL-1B | 50 ug | | | |
| | silastic | 250 ul | | | |
| | lipase | 2.0 mg | I.M | R/h quart | Day 7 |
| | TiterMax | 500 ul | | | Day 14 |
| | saline | 500 ul | | | Day 21 |
| Group 5—CRD & nasal | | | | | |
| | lipase | 1 mg | CRD | RH groin | Day 0 |
| | mannitol | 13 mg | | | |
| | sod citrate | 13 mg | | | |
| | IL-1B | 50 ug | | | |
| | silastic | 250 ul | | | |
| | lipase | 1 mg | nasal | nostril | Day 7 |
| | C/Tox | | | | Day 14 |
| | saline | 2.5 ml | | | Day 21 |
| Group 6—CRD minus Adj | | | | | |
| | lipase | 1 mg | CRD | RH groin | Day 0 |
| | mannitol | 13 mg | | | |
| | sod citrate | 13 mg | | | |
| | silastic | 250 ul | | | |

Figure 7:
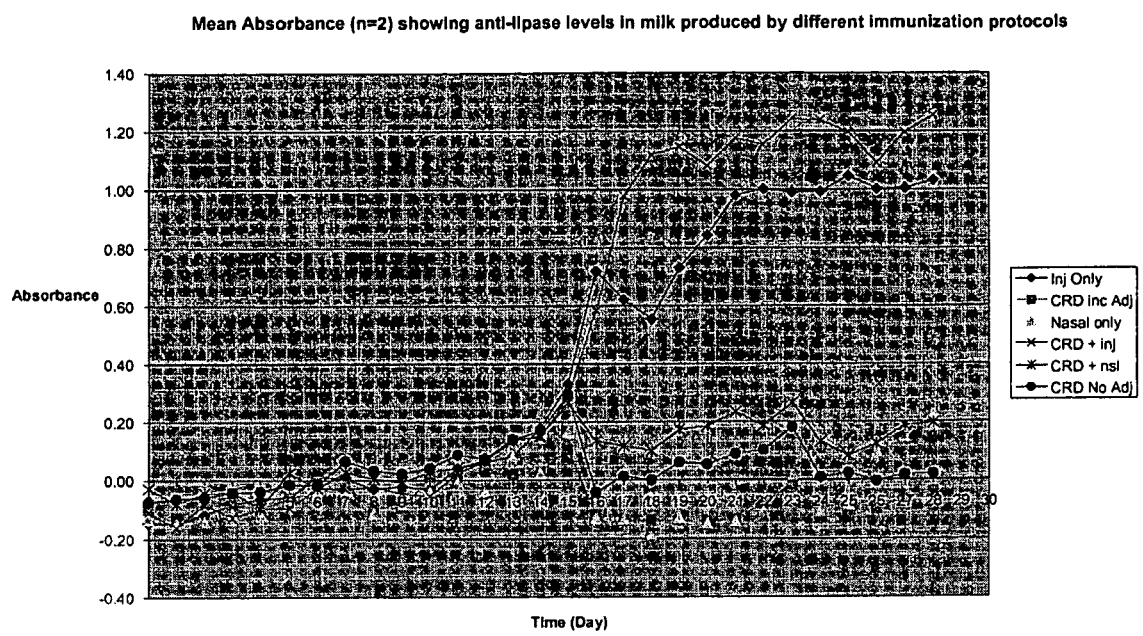
FIG. 7 shows a graph of the level of anti-lipase antibodies in milk from goats immunized with different protocols. The level of anti-lipase antibodies in milk from goats immunized with different protocols. The mean absorbance values of two animals were plotted over 28 days for each protocol. Maximum antibody levels were achieved with the procedure using an antigen releasing device (CRD) and intramuscular injection.

A total of 12 goats were studied, with two goats dedicated to each inoculation regime. The presence of anti-lipase antibodies was evaluated with Enzyme-Linked Immunosorbent Assay (ELISA). The mean absorbance value less that of the blank control of the daily milk samples were plotted (FIG. 7). Results were reproducible between animals, as shown in FIG. 7.

All six regimens were successful in raising antibodies. However, the relative concentrations of antibodies for each group varied. The highest mean absorbance value; which is indicative of the greatest concentration of antibodies produced; was recorded for the Group 4 animals. The Group 4 animals received an ARD implant on Day 0 of the program and 3 subsequent injections to the back flank area on Days 7, 14 and 21.

The mean absorbance value of Group 4 was greater than the value produced by the Group 1 goats, who only received 1 M injections at day 7, 14 and 21.

Both Group 1 and 4 animals showed some response up to approximately Day 14. At Day 15, the levels of anti-lipase antibodies increased substantially, presumably a consequence of the secondary immune response. The higher levels of antibodies were sustained for the duration of the study, in this case up to Day 28.

Figure 8:
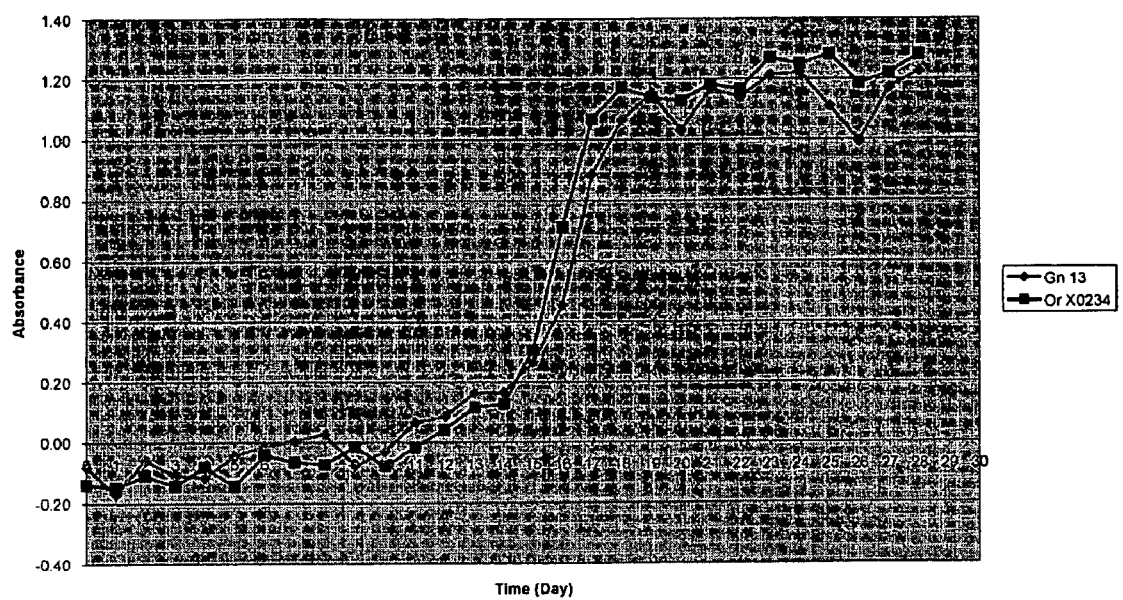
FIG. 8 shows a graph of the individual absorbance levels of anti-lipase antibodies in two separate animals implanted with an antigen releasing device (ARD) and given intramuscular injections. The levels of anti-lipase antibodies in two separate animals implanted with an antigen releasing device (CRD) and given intramuscular injections. The two results highlight the reproducible nature of the immunization procedure.
Figure 9:
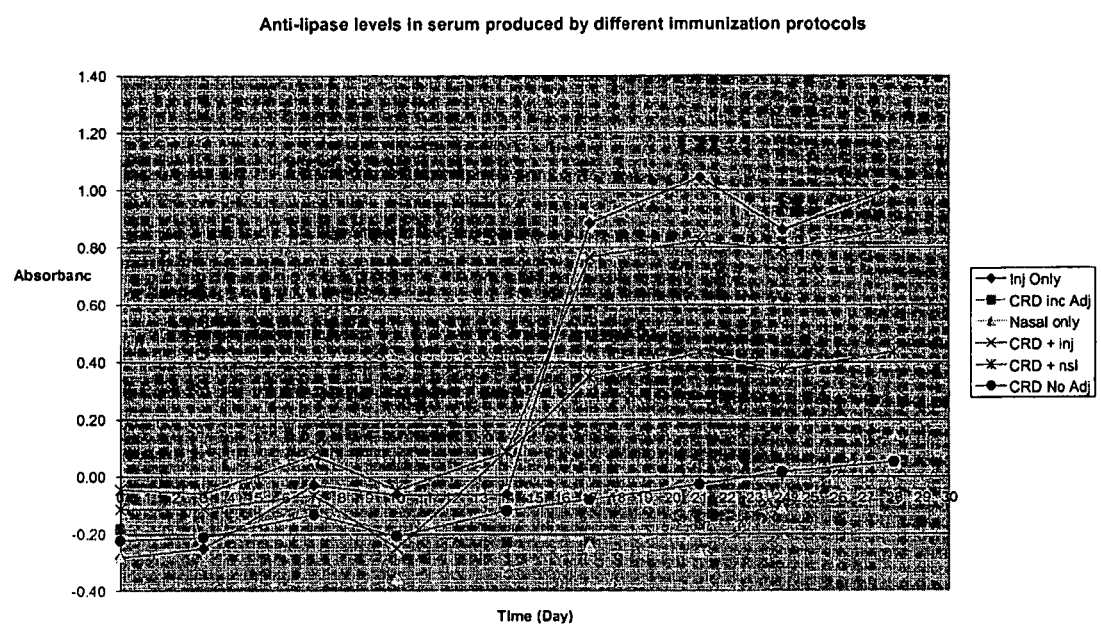
FIG. 9 shows a graph of the level of anti-lipase antibodies in serum from goats immunized with different protocols. The mean absorbance values of two animals were plotted over 28 days for each protocol.
Figure 10:
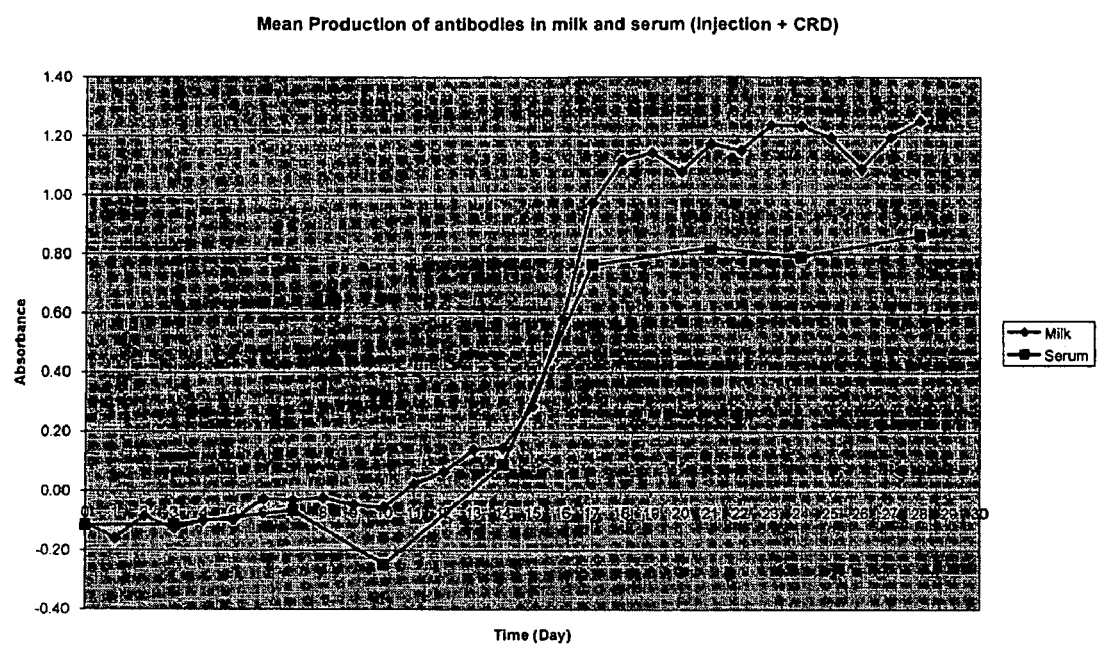
FIG. 10 shows a comparison of mean anti-lipase anti-body levels in milk (♦) and serum (■) produced by immunization of goats with an antigen releasing device (ARD) and intramuscular injection.
Figure 11:
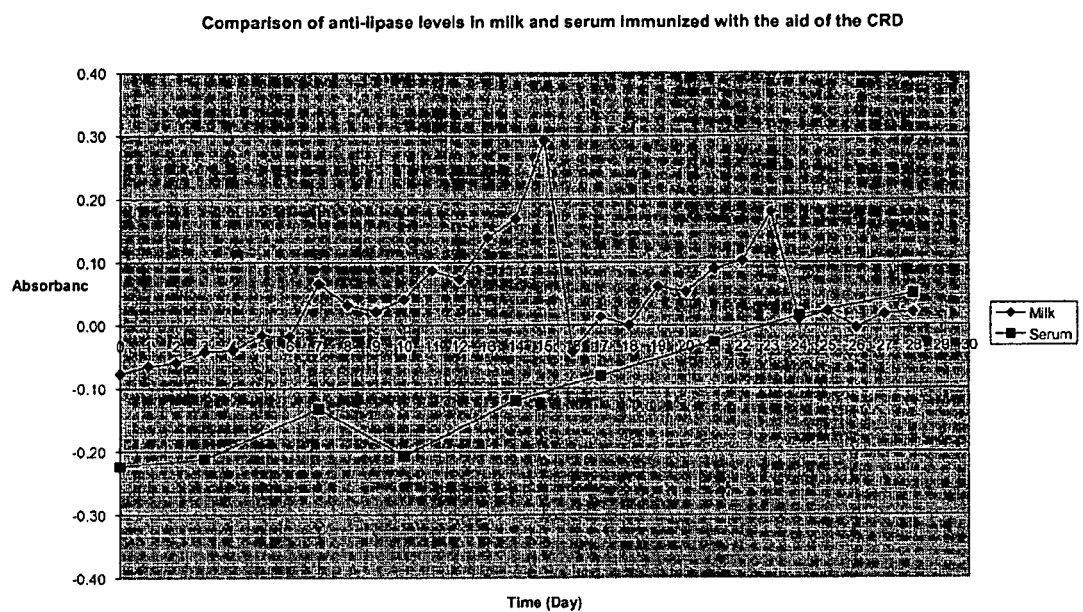
FIG. 11 shows a graph of anti-lipase antibody production in milk (♦) and serum (■) in goats implanted with an antigen releasing devices. The level of anti-lipase antibody levels in milk and the absence of anti-lipase antibodies in serum suggest that the antigens in the antigen releasing device implanted in the groin area are diffusing into the supramammary lymph node.

The levels of anti-lipase antibodies in the serum of the inoculated animals was also measured, as shown in FIGS. 8, 9 and 10. FIG. 8 shows results of the individual absorbance levels of anti-lipase antibodies in two separate animals implanted with an antigen releasing device (ARD) and given intramuscular injections. FIG. 9 shows results of the level of anti-lipase antibodies in serum from goats immunized with different protocols. FIG. 10 shows results of a comparison of mean anti-lipase anti-body levels in milk and serum produced by immunization of goats with an antigen releasing device (ARD) and intramuscular injection. FIG. 11 shows the anti-lipase antibody production in milk and serum in goats implanted with an antigen releasing devices. The level of anti-lipase antibody levels in milk and the absence of anti-lipase antibodies in serum suggest that the antigens in the antigen releasing device implanted in the groin area are diffusing into the supramammary lymph node.

Example 11

Immunization Protocol 4

The protocol used two lactating goats (*Capra hircus*) for each group, with four goats used in total. The antigen used was lipase from *Pseudomonas fluorescens*.

Preparation for by Immunization Protocol
1. Emulsify 30 mg of lipase in 15 ml 0.85% saline.
2. Emulsification with Titermax Gold was according to manufacturer's specification. The lipase in saline solution was mixed with an equal volume of Titremax Gold (1:1).
3. Dispense 1 ml into 2.5 ml syringe for administration. (Each 1 ml dose contains 1 mg lipase)
4. Two groups of animals were inoculated on Day 0, 10 and 19.
5. Group 1 was inoculated in the left flank and Group 2 was inoculated adjacent to the supramammary lymph node.
6. Milk and serum was collected.

Coating plates for Enzyme Linked Immunosorbent Assay (ELISA)
1. Prepare 2.5 µg/ml of antigen in coating buffer.
2. 100 µl of the mixture was dispensed into each well of a 96 well ELISA tray.
3. The plates were covered and were left to stand overnight at 4° C.

Enzyme Linked Immunosorbent Assay (ELISA) Protocol
1. Prior to use, the coated plates were washed 3 times with PBS Tween.
2. A serum diluent of 1% Human serum in PBS Tween.
3. Load 100 µl of the serum diluent into each well.
4. Load 1 µl of sample of interest to well.
5. Plates were incubated at 37° C. for 2 hours.
6. Plates were washed 3 times with PBS Tween.
7. 1/1000 dilutions of mouse α-sheep IgG, mouse α-sheep IgA and mouse α-sheep IgM in 1% serum diluent (1% Human serum in PBS Tween) were prepared.
8. Load 100 µl Into respective wells.
9. The plates were placed in 37° C. for 2 hrs.
10. The plates were washed 3 times with PBS Tween.
11. 1/2500 dilution of rabbit α-mouse IgG (H+L) in 1% serum diluent was prepared.
12. Load 100 µl per well.
13. Incubate at 37° C. for 2 hrs.
14. The plates were washed 3 times with PBS Tween.
15. A 1/100 dilution of 250 mg/ml Nitrophenyl phosphate in Diethanolamine Buffer was prepared.
16. Load 100 µl per well.

17. Incubate at room temperature for approximately 20 to 30 minutes.
18. The reaction was terminated with 50 ul of 3.75 M NaOH.
19. ELISA plates were read at 405 nm.

Results

Figure 13:
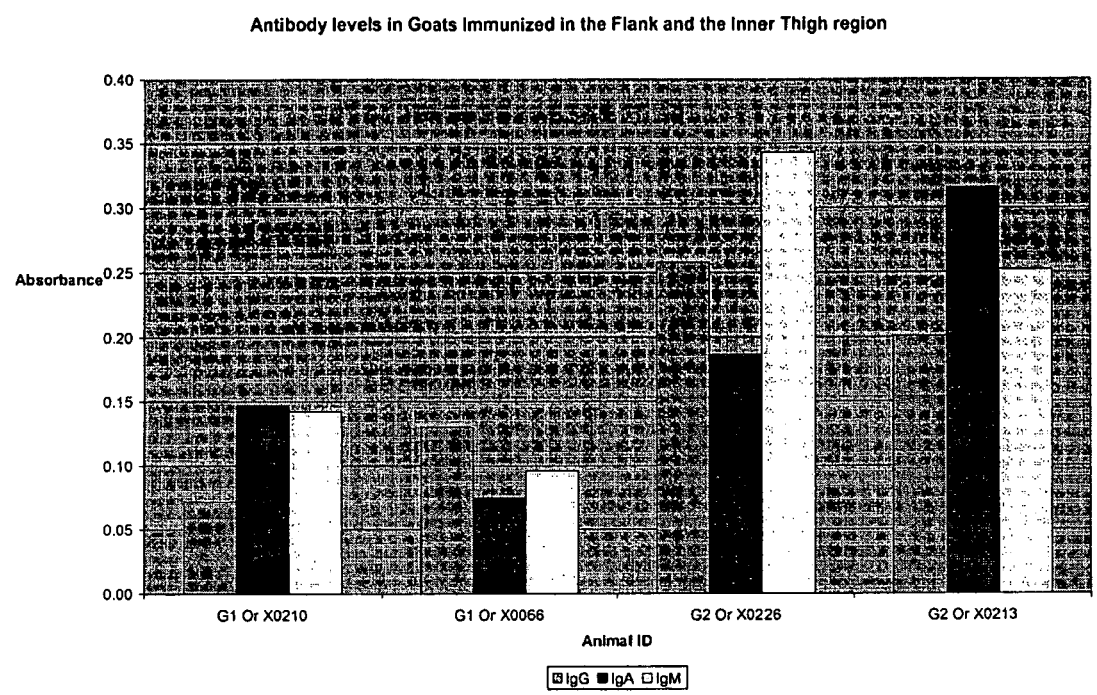
FIG. 13 shows a graph of the levels of IgG, IgA and IgM in the milk of goats inoculated with lipase from *Pseudomonas fluorescens*. Two groups of animals were inoculated in different locations (Group 1 (G1) into the flank and Group 2 (G2) in the region adjacent to the supramammary lymph nodes) on Days 0, 10 and 19. The relative levels of IgG, IgA and IgM were determined by ELISA. The levels of all three classes of immunoglobulins were higher in the milk of Group 2 animals when compared to Group 1 animals.

Milk collected was analyzed by ELISA for levels of IgG, IgA and IgM. Results from Group 1 (intermuscular into the flank—designated G1) and Group 2 (stimulation of the supramammary lymph node—G2 animals) in FIG. 13 shows higher levels of all three classes of immunoglobulin produced in the milk of Group 2 animals when compared to Group 1 animals.

Example 12

Collection and Storage of Milk Samples

Materials
(i) Beckman Acuspin Refrigerated Centrifuge
(ii) Rennet Type II from *Mucor meihel* (Sigma) in Hp water at a concentration of 2 mg/ml
(ii) 10 ml sterile centrifuge tubes
(iv) P1000 pipetteman
(v) 1 ml disposable transfer pipettes
(vi) 5 ml plastic storage tubes
(vii) 37° C. incubator Method Milk was collected by hand milking into 32 ml glass McCartney bottles in the absence of any chemical or mechanical stimuli. Milk was generally collected in the morning without prior separation from kids. Samples were stored on ice after collection and transferred as soon as practicable thereafter. Milk was transferred to sterile 10 ml centrifuge tubes and centrifuged at 2000 rpm for 15 mins at 4° C. Milk was aspirated from under the solid fat layer using disposable pipette and placed in fresh 10 ml tube. The pipette was carefully plunged through the fat layer into the milk layer below. 2 mg/ml Rennet solution was added to the milk at the ratio of 0.4 ml rennet to 5 ml milk, tubes were shaken then incubated at 37° C. for 1 to 2 hours. Tubes were centrifuged at 5000 rpm×15 mins at 4° C. Supernatant was removed by transfer pipette and stored at −20° C.

Antibodies in the milk were quantified by the Enzyme-Linked Immunisorbent Assay (ELISA). The absorbance values, which are indicative of relative concentrations of the anti-lipase antibody, for serum were lower when compared to milk. The levels of anti-lipase antibodies produced in the milk were higher when compared to antibody levels in serum.

Example 13

Collection and Storage of Blood Samples

Materials
(i) 7 ml of 9 ml Vacutainers™ (Bectco Dickinson) for serum collection
(ii) 20G×1.5 inch Vacutainer™ (Bectco Dickinson) needles and holder Methods Blood samples were taken from the jugular vein using Vacutainer™ collection tubes, holder and needle. Tubes were stored at 4° C. Samples were centrifuged at 4000 rpm×15 min at 4° C. Upper serum layer was removed using a transfer pipette and stored at −20° C.

Example 14

Enzyme-Linked Immunosorbent Assay (ELISA)

Materials
(i) 10× Phosphate Buffer Saline (PBS); 1 L double distilled water, 1.91 g $KH_2PO_4$ (BDH Chemicals Aust Pty Ltd), 6.1 g $Na_2HPO_4$ (ASAX Chemicals), 2 g KCl (BDH Chemicals Aust Pty Ltd),
(ii) 80 g NaCl, 1.95 g $NaN_3$ (Sigma Aldrich), pH to 7.4
(iii) 200 ml Carbonate coating buffer pH 9.6 containing; 200 ml double distilled water, 3.18 g $Na_2CO_3$ (BDH), 5.88 g $NaHCO_3$ (BDH), 0.39 g $NaN_3$ (Sigma).
(iv) 0.85% saline (Excel laboratories)
(v) 0.25 mg/ml lipase from *P. fluorescens* (Sigma Aldrich) in carbonate coating buffer
(vi) PBS-TW20 plate washing solution (BDH); 200 ml 10×PBS (as above), 1800 ml distilled water, 1 ml Tween-20 (Labchem)
(vii) Serum diluent; 200 ml glycerol (BDH), 29 g NaCl (BDH), 0.2 g $KH_2PO_4$ (BDH), 0.61 g $Na_2HPO_4$ (BDH), 0.2 g KCl (BDH), 1.95 g $NaN_3$ (Sigma), distilled water to 1 L, 1.5 ml Tween-20 (Labchem), pH to 7.4. Store 4° C. Dessicated BSA (CSL) added to desired aliquot at 1% concentration, prior to use.
(viii) Saline 0.85% (Excel Laboratories)
(ix) Donkey anti-goat IgG-Horse Radish Peroxidase (HRP) (Promega)
(x) 1 M $H_2SO_4$ (AJAX Finechem)
(xi) TMBS EIA solution (BioRad) Part A & B
(xii) P200 pipetteman and tips
(xiii) P20 pipetteman and tips
(xiv) nunc™ polsorb 96 well ELISA plates
(xv) BioRad™ 96 well plate spectrophotometer model 450

Methods

100 µl of lipase in carbonate buffer added to wells of ELISA plate and stored at 4° C. overnight. Plates were washed 3 times with PBS-TW. 100 µl of serum diluent was added to wells for serum analysis, and 90 µl were added to wells for milk analysis. 1 µl of serum sample and 10 µl of milk sample added to the serum diluent. The mixture was created by gentle tapping the plate. The plates were stored at 4° C. overnight. The plates were washed 3 times with PBS-TW. 100 µl of a 1/2500 dilution of Donkey anti-goat IgG-HRP in 0.85% saline added to each well. The plates were incubated at room temperature for 1 hour. The plates were washed 3 times with PBS-TW. 9 Part A and 1 part B of TMBS were mixed in a glass Schott bottle and 100 µl was added to each well. The plates were incubated at room temperature for 10 minutes. 100 µl 1 M $H_2SO_4$ was added to each well and plate read on spectrophotometer at 450 nm. A printout of the absorbance results was obtained. The absorbance values of each milk and blood sample collected from all animals were measured. Plots of absorbance values on the y-axis against time (days) on the x-axis were prepared for individual animals and the average absorbance value for each group (comprising two test subjects).

Example 15

Lipase Diffusion in Milk Agar Slide
(i) Prepare 1% (1 g/100 ml) agar (Oxoid Cat No L13, Basingstoke, Hampshire, England) in Phosphate Buffer Saline (pH 7.4).
(ii) Add 100 µl of whole milk (Masters, Perth, Australia) to 5 ml 1% agar.

(iii) For slide format, 2.5 ml of 'milk agar' is poured over the glass and allowed to set for 10 minutes (2% milk in 1% agar).
(iv) Five 1.5 mm diameter holes in the milk agar gel were prepared with an agar punch and the agar removed by vacuum.
(v) The agar film was incubated over night with lipase from *P. fluorescens* (Aldrich, Milwaukee, Wis., USA). 5 mg/ml of lipase was prepared in 0.85% saline.
(vi) The diffusion zone, indicative of lipid degradation of the lipase test was compared to plate with (a) saline, (b) lipase+ antibody negative serum and (c) lipase+anti-lipase positive serum.

Figure 12:
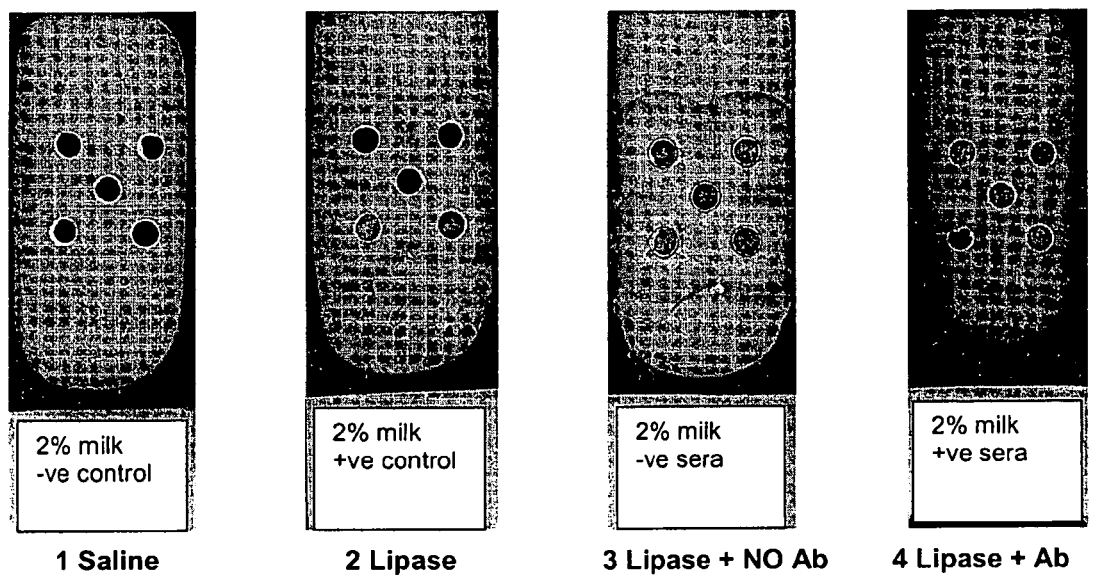
FIG. 12 shows photographs of a diffusion assay of milk agar on glass slides illustrating the inhibitory effects of anti-lipase antibodies on the lipolytic activity of the lipase enzyme. Slide 1: PBS or saline was added to the wells. Slide 2: 5 mg/ml lipase from *P. fluorescens*. Slide 3: 5 mg/ml of lipase with an antibody negative serum (1:1 dilution). Slide 4: 5 mg/ml of lipase with serum that was positive for anti-lipase antibodies (1:1 dilution).

Results are present in FIG. 12. On each milk slide, 5 wells were filled with saline (slide 1), the lipase enzyme (slide 2), lipase with an antibody negative serum (slide 3) and lipase with an anti-lipase antibody positive serum (slide 4). In slide 2, a zone of hydrolysis is visible as the lipase enzyme hydrolyzes the lipids in the milk film. The negative control (saline in slide 1) confirms that the enzyme is responsible for the zone of hydrolysis. The hydrolysis activity of the lipase enzyme can be inhibited by an anti-lipase antibody, as evident in slide 4. Slide 3 which contains an antibody negative serum confirms that it is the antibody and not other components of serum that is inhibiting the enzyme.

Although the invention has been described with reference to certain preferred embodiments, it will be appreciated that many variations and modifications may be made within the scope of the broad principles of the invention. Hence, it is intended that the preferred embodiments and all of such variations and modifications be included within the scope and spirit of the invention.

The claims defining the invention are as follows:

1. A method for inducing the sustained release of antibodies in milk comprising the step of:
   a) administering a primer composition adjacent to, within close proximity of or within at least one supramammary lymph node;
   b) implanting at least one antigen releasing device adjacent to, within close proximity of or within at least one supramammary lymph node; and
   c) administering at least one or more booster compositions comprising antigen to a mammal adjacent to, within close proximity of or within at least one supramammary lymph node after the antigen releasing device has been implanted; wherein the primer composition, the antigen releasing device and the one or more booster compositions each comprise the same antigen and wherein the antigen releasing device releases the antigen into the tissue area around the supramammary lymph node which stimulates antibody secretion into a mammary gland.

2. The method of claim 1 wherein the antigen releasing device is located in sufficient proximity to the supramammary gland such that the release of antigen from the antigen releasing device induces the production of antibodies in milk over the life of the antigen releasing device.

3. The method of claim 2 wherein the antigen releasing device is implanted at a distance of up to 100 mm from at least one supramammary lymph node.

4. The method of claim 3 wherein the antigen releasing device is implanted at a distance of between about 1 mm and 100 mm from at least one supramammary lymph node.

5. The method of claim 4 wherein the antigen releasing device is implanted at a distance of between about 50 mm and 100 mm from at least one supramammary lymph node.

6. The method of claim 1 wherein the antigen releasing device is implanted in a mammal selected from the group comprising: rodents goats, sheep and cattle.

7. The method of claim 6 wherein the device is implanted in a dairy cattle, dairy goat or dairy sheep breed.

8. The method of any one of claims 2-6 and 7, wherein the antigen is a bacterial antigen.

9. The method of claim 8 wherein the bacterial antigen is from a bacterial genus selected from: *Escherichia, Staphylococcus, Streptococcus, Salmonella* and *Helicobacter*.

10. The method of claim 8 wherein the bacterial antigen is from a bacterial species selected from: *Escherichia coli, Clostridium difficile, Vibrio cholerae* and *Helicobacter pylori* and *Pseudomonas fluorescens*.

11. The method of claim 8 wherein the bacterial antigen is lipoprotein lipase from *Pseudomonas fluorescens*.

12. The method of claim 1 wherein the antigen releasing device allows the antigen contained therein to be released from the device at a rate which causes the antibody response of the mammal into which it is implanted to be maintained at a desirable level.

13. The method of claim 1 wherein administration of the primer composition takes place before implanting the antigen releasing device.

14. The method of claim 1 wherein administration of the primer composition takes place during implantation of the antigen releasing device.

15. The method of claim 1 where the primer composition is delivered to a mucosal surface.

16. The method of claim 1 wherein the primer composition is administered in a single administration.

17. The method of claim 1 wherein the primer composition is administered in a number of administrations at intervals over a period of days or weeks.

18. A method according to claim 1 wherein the booster composition is delivered to a mucosal surface.

19. The method of claim 1 wherein the booster composition is administered in a single administration.

20. The method of claim 1 wherein the booster composition is administered in a number of administrations at intervals over a period of days or weeks.

21. The method of claim 1 wherein the antigen releasing device, the primer composition and the booster composition further comprise an adjuvant.

22. A method of claim 1 for the production of mammalian milk containing antibodies comprising the steps of: a) induction of antibodies according to the method of claim 1; and b) collecting the antibody containing milk from the mammal.

23. The method of claim 22 wherein the milk is used in the form obtained directly from the mammal.

24. The method of claim 22 wherein the milk is processed prior to use.

25. The method of claim 24 wherein the method of processing is selected from the list comprising: heat treatment, ultra violet radiation, concentration, supplementation with food additives and drying into concentrates or milk powders.

26. The method of claim 22 comprising the further step of isolating the antibodies from the milk.

27. The method of claim 26 wherein the antibodies are purified after isolation.

28. A method for producing protein concentrates containing antibodies comprising the steps of: a) collecting the milk of milk-bearing female mammals implanted with antigen releasing device according to the method of claim 1; b) separating the cream and the impurities; c) coagulating the clarified and skimmed milk; d) separating the casein; e) filtering, ultrafiltering and sterilizing the proteins of the whey; f)

evaporating and drying the proteins under conditions which do not denature the antibodies and which maintain sterility.

29. A method for inducing the sustained release of antibodies in milk, comprising the steps of:
   a) administering a primer composition adjacent to, within close proximity of or within at least one supramammary lymph node;
   b) implanting at least one antigen releasing device adjacent to, within close proximity of or within at least one supramammary lymph node; and
   c) administering at least one or more booster compositions comprising antigen to a mammal adjacent to, within close proximity of or within at least one supramammary lymph node after the antigen releasing device has been implanted;

wherein the primer composition, the antigen releasing device and the one or more booster compositions each comprise the same antigen and wherein the antigen releasing device releases the antigen into the tissue area around the supramammary lymph node which stimulates antibody secretion into a mammary gland and wherein the method further comprises a preselection step prior to administration of the antigen releasing device.

\* \* \* \* \*